United States Patent [19]

Badolato et al.

[11] Patent Number: 4,975,247
[45] Date of Patent: Dec. 4, 1990

[54] MASS TRANSFER DEVICE HAVING A MICROPOROUS, SPIRALLY WOUND HOLLOW FIBER MEMBRANE

[75] Inventors: Anthony Badolato, Willingboro, N.J.; James G. Barrera, Audubon; Edmund R. Corey, Jr., Schwenksville, both of Pa.

[73] Assignee: Medtronic, Inc., Minneapolis, Minn.

[21] Appl. No.: 124,356

[22] Filed: Nov. 19, 1987

Related U.S. Application Data

[63] Continuation of Ser. No. 806,378, Dec. 12, 1985, abandoned, which is a continuation-in-part of Ser. No. 689,613, Jan. 8, 1985, abandoned.

[51] Int. Cl.$^5$ .............................. A61M 1/14
[52] U.S. Cl. ........................ 422/48; 422/46; 210/321.74; 210/321.79; 210/321.83; 210/321.88; 210/497.1; 128/DIG. 3
[58] Field of Search ............ 422/45, 46, 48; 210/321.74, 321.79, 321.83, 321.88, 497.1; 128/DIG. 3; 29/820, 234, 240, 240.5, 428, 456, 455.1; 242/7.02

[56] References Cited

U.S. PATENT DOCUMENTS

| | | | |
|---|---|---|---|
| 3,422,008 | 1/1969 | McLain | 210/321.5 X |
| 3,536,611 | 10/1970 | DeFilippi et al. | 210/646 |
| 3,794,468 | 2/1974 | Leonard | 422/48 |
| 4,105,548 | 8/1978 | Baker et al. | 210/23 H |
| 4,224,094 | 9/1980 | Amicel et al. | 156/169 |
| 4,239,729 | 12/1980 | Hasegawa et al. | 422/48 |
| 4,352,736 | 10/1982 | Ukai et al. | 210/497.1 X |
| 4,368,124 | 1/1983 | Brumfield | 210/321.3 |
| 4,374,802 | 2/1983 | Fukasawa | 422/48 |
| 4,424,190 | 1/1984 | Mather, III et al. | 422/46 |
| 4,430,219 | 2/1984 | Kuzumoto et al. | 210/321.3 |
| 4,490,331 | 12/1984 | Steg, Jr. | 422/46 |
| 4,572,446 | 2/1986 | Leonard et al. | 242/7.02 |
| 4,622,206 | 11/1986 | Torgeson | 422/48 |
| 4,639,353 | 1/1987 | Takemura et al. | 422/46 |
| 4,645,645 | 2/1987 | Martinez et al. | 422/46 |
| 4,659,549 | 4/1987 | Hamada et al. | 422/48 |

Primary Examiner—Robert J. Warden
Assistant Examiner—L. Kummert
Attorney, Agent, or Firm—Reed A. Duthler

[57] ABSTRACT

A hollow fiber oxygenator including a hollow fiber bundle having first and second ends located within an oxygenator chamber. The oxygenator chamber includes a hollow core around which the hollow fibers are spirally wound and includes an outer casing adjacent the fibers. A gas entry port is coupled to the interior of the fibers adjacent the first end of the bundle and a gas outlet is coupled to the interior of the fibers at the second end of the bundle. A blood inlet to the oxygenator chamber, exterior of the fibers, is provided adjacent the second end of the bundle, and a blood outlet from the oxygenator chamber is provided adjacent the first end of the bundle. The resulting structure provides an axial flow oxygenator, in which the direction of blood flow through the oxygenator chamber is opposite the direction of gas flow through the fibers.

13 Claims, 13 Drawing Sheets

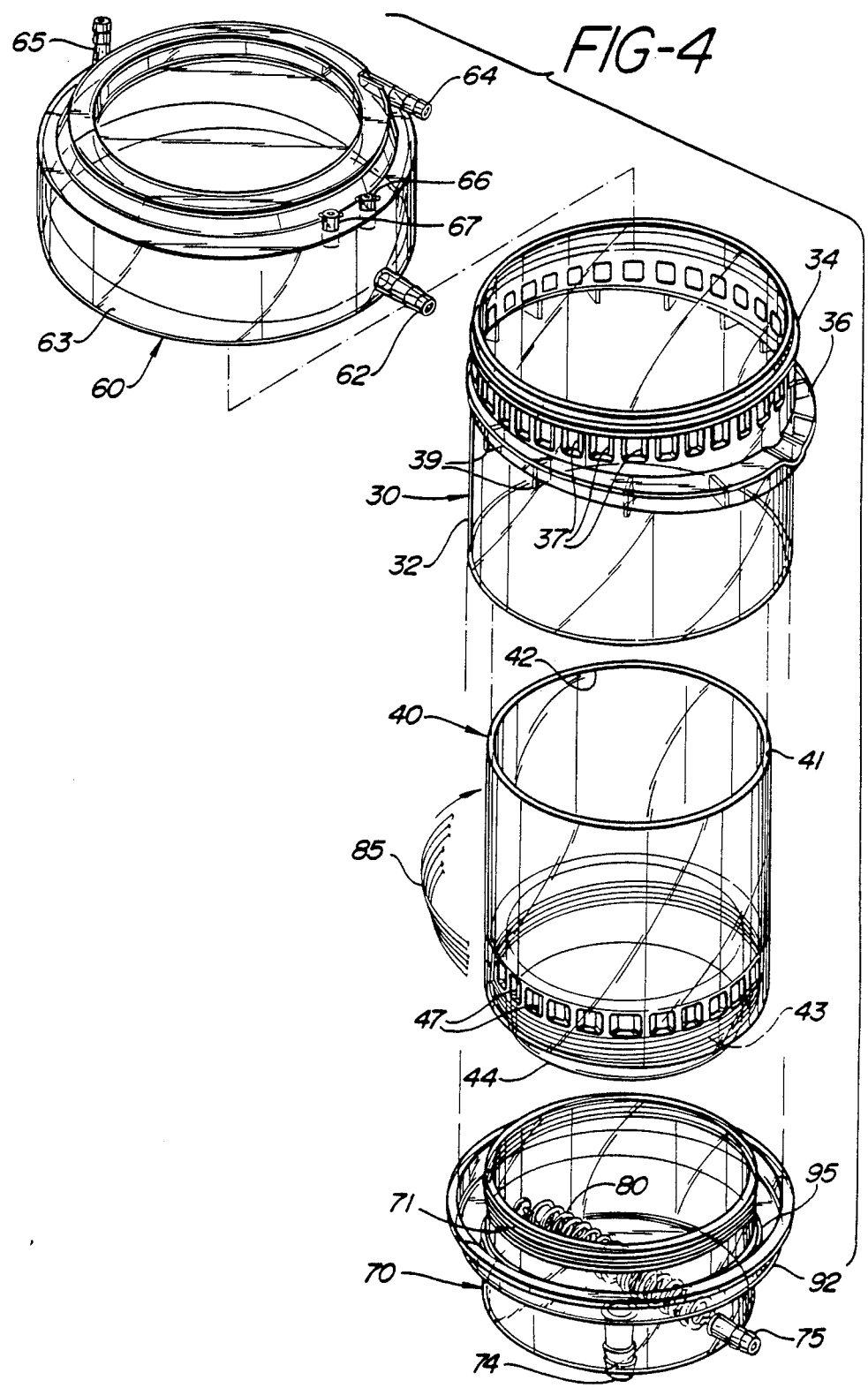

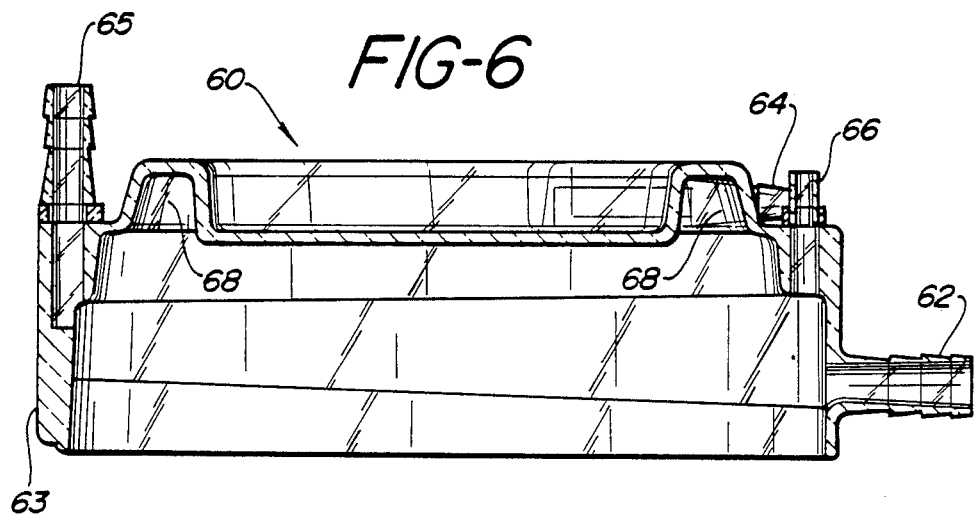
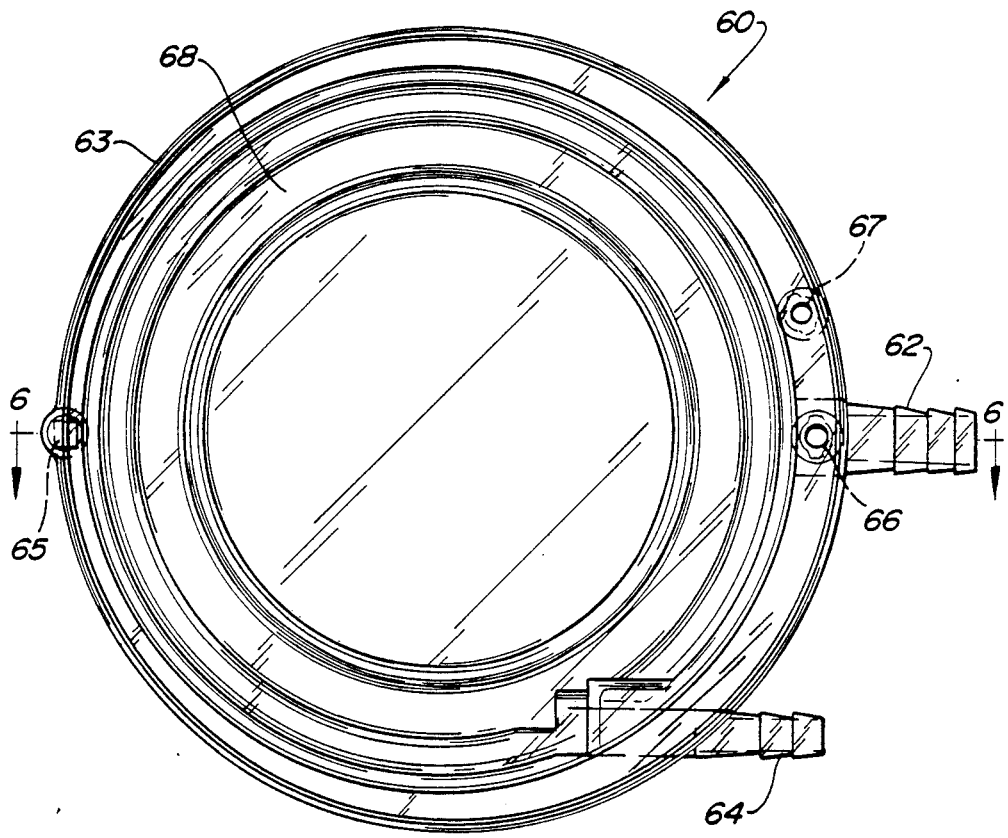

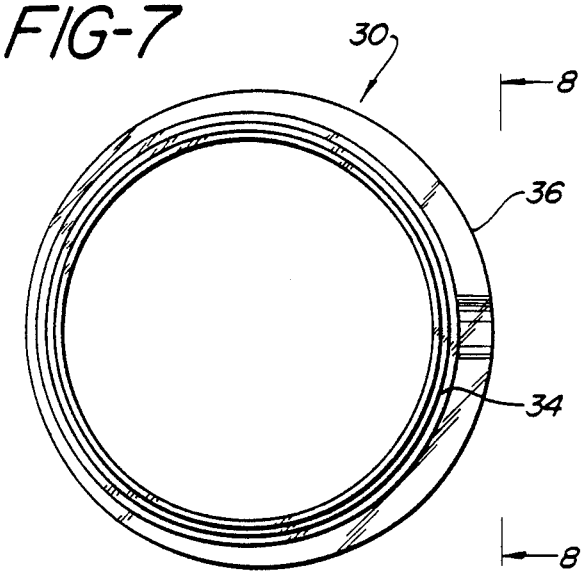
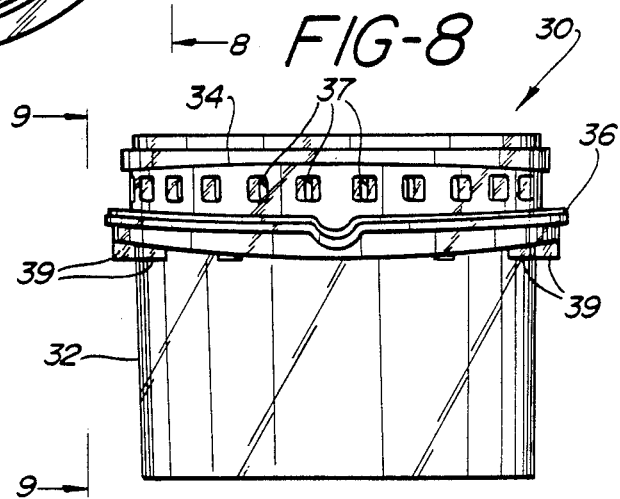
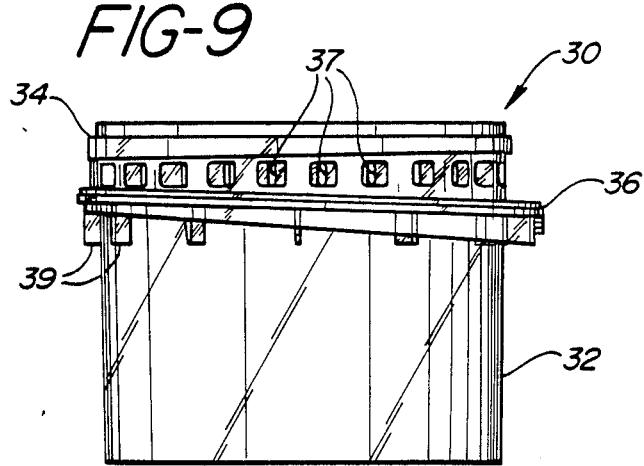

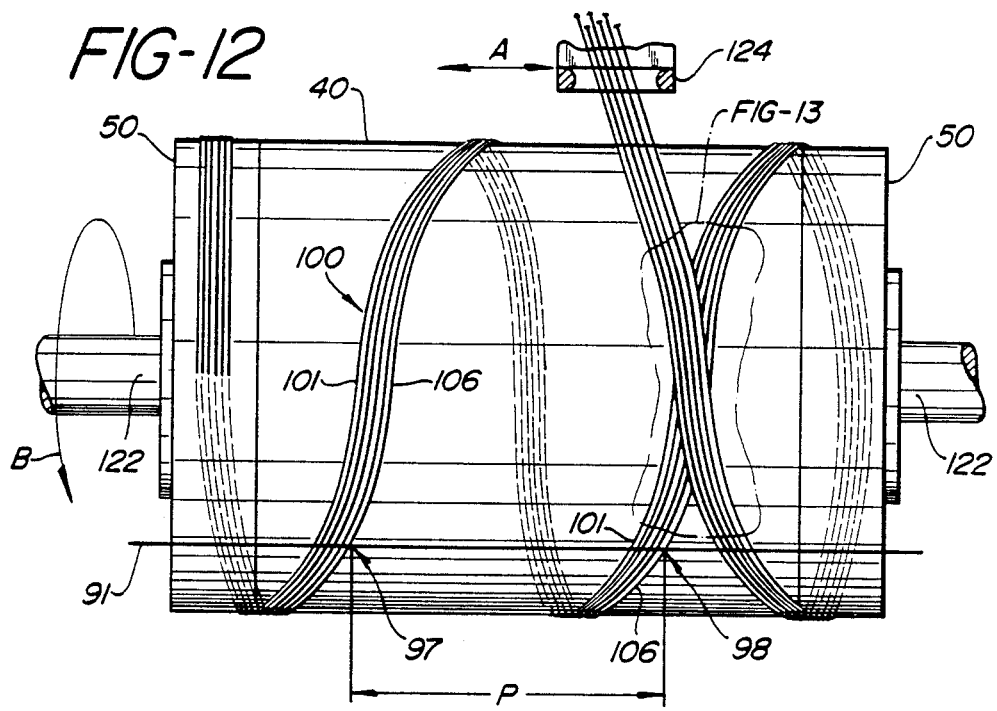
FIG-12
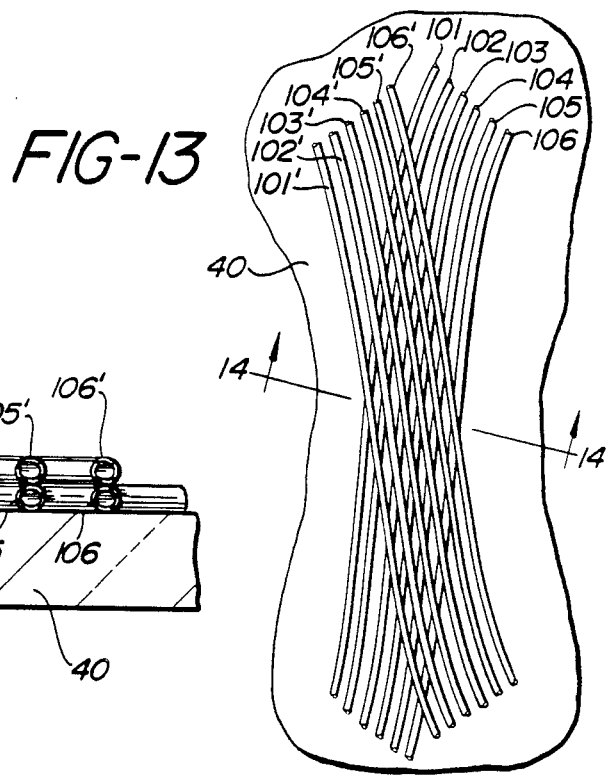
FIG-13
FIG-14

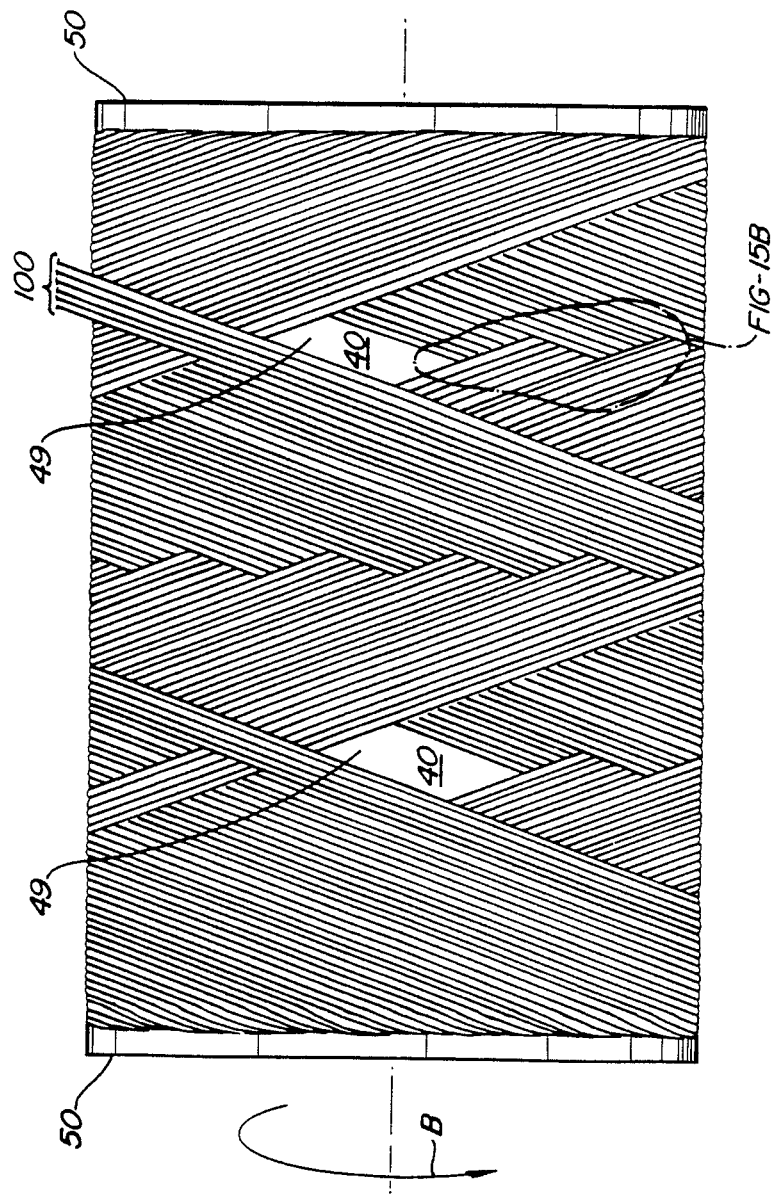

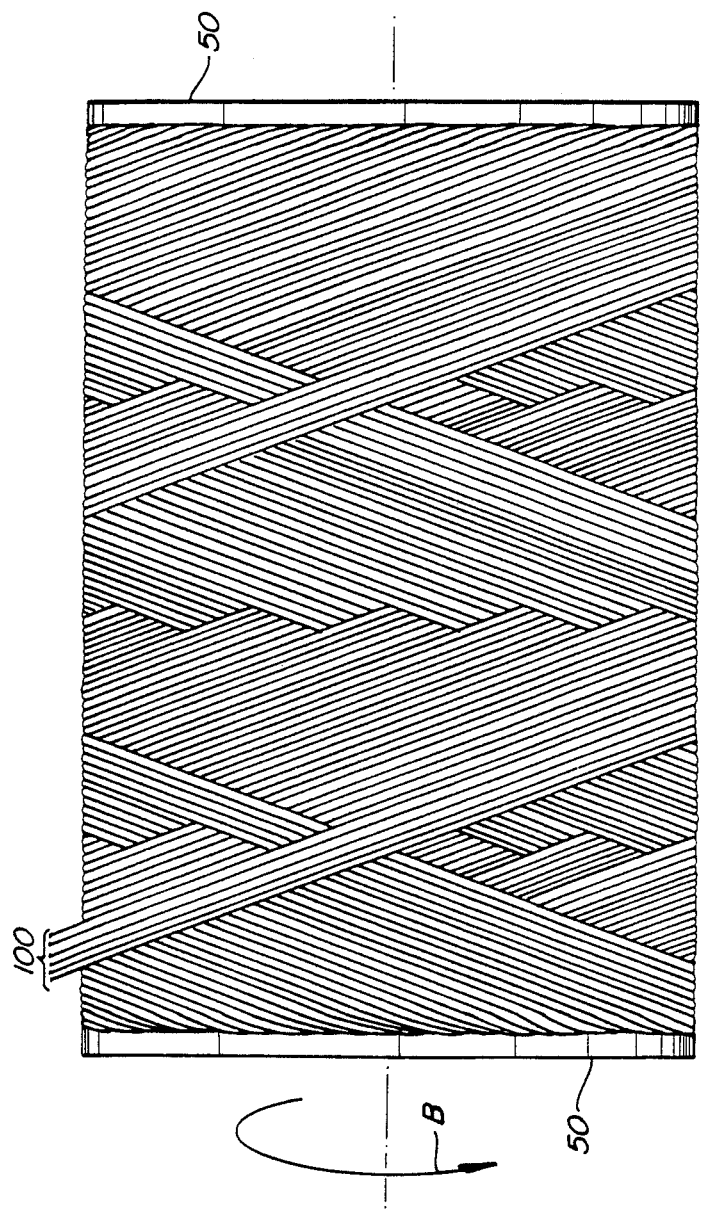

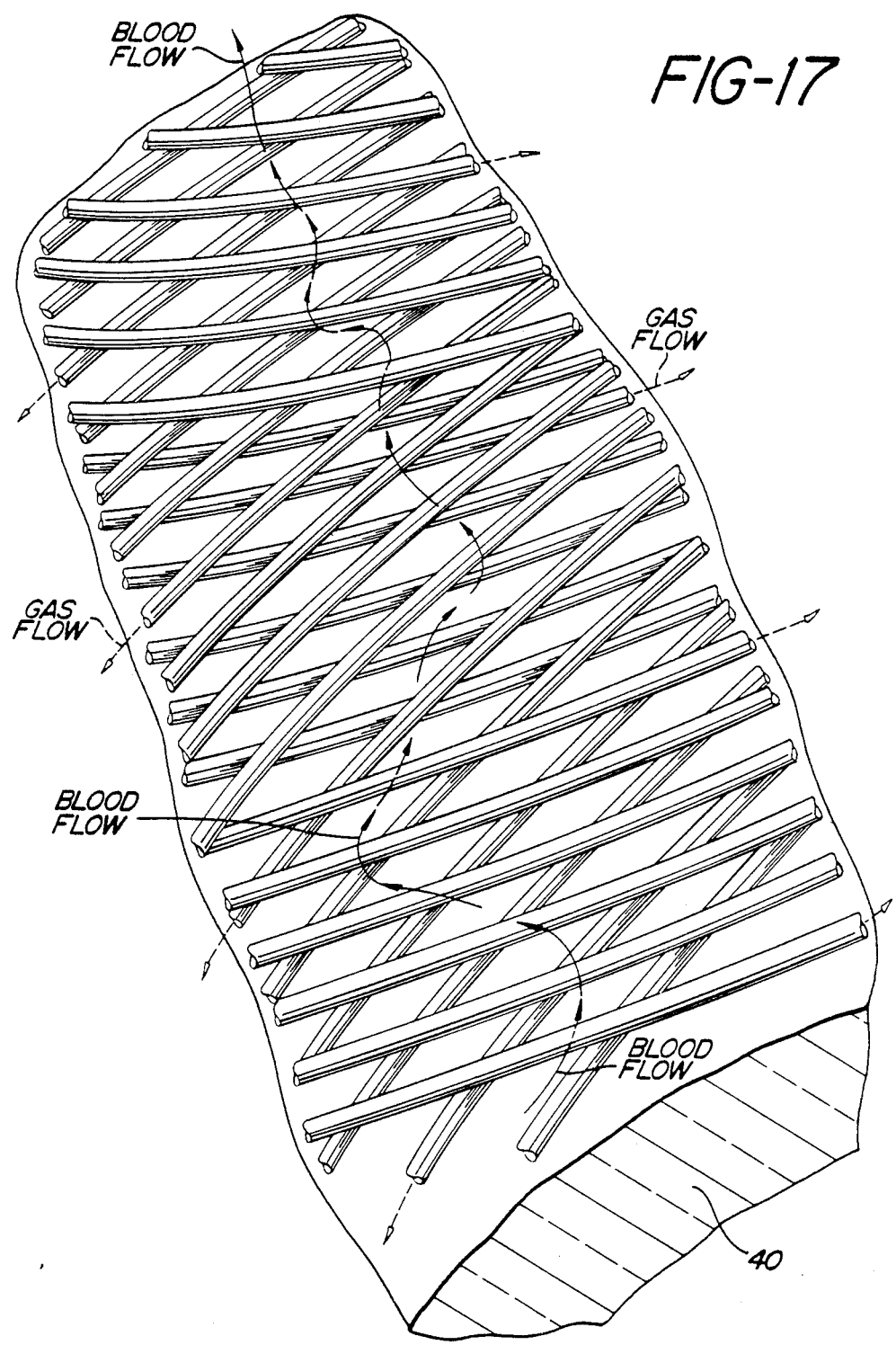

MASS TRANSFER DEVICE HAVING A MICROPOROUS, SPIRALLY WOUND HOLLOW FIBER MEMBRANE

This is a continuation of co-pending application Ser. No. 806,378, filed on Dec. 12, 1985, which is a continuation-in-part of U.S. Ser. No. 689,613, filed Jan. 8, 1985, both now abandoned.

FIELD OF THE INVENTION

The present invention relates to a mass transfer device in which substances contained in fluids flowing on opposite sides of a microporous membrane are exchanged for each other by molecular transfer across that membrane. More particularly, the invention relates to a mass transfer device in which the microporous membrane comprises a plurality of spirally wound, microporous hollow fibers. Even more particularly, the invention relates to an axial flow, spirally wound hollow fiber blood oxygenator and to a method for extracorporeally oxygenating the blood of an animal or human.

BACKGROUND OF THE INVENTION

Blood oxygenator systems have been used for some time now in open heart surgery and for providing emergency cardiopulmonary assistance. In both instances, the oxygenator takes over, either partially or completely, the normal gas exchange function of the patient's lung. In oxygenators which employ a microporous membrane, blood is taken from the patient and is circulated extracorporeally through the oxygenator on one side of the membrane. Concurrently, an oxygenating gas is passed through the oxygenator on the other side of the membrane. Carbon dioxide is transferred from the blood across the microporous membrane into the passing stream of oxygenating gas; at the same time, oxygen is transferred from the oxygenating gas across the membrane into the blood. The circulating blood, having thereby been reduced in carbon dioxide content and enriched in oxygen, is returned to the patient. Blood is circulated, oxygenated and returned to the patient in the aforementioned manner until the patient's own cardiopulmonary system is once more able to carry out its normal circulatory and gas exchange functions.

Several types of blood oxygenators have been or are generally available. One type is a bubble oxygenator wherein the oxygenating gas is introduced into the blood directly in the form of bubbles. In a second type of oxygenator, called a film-type oxygenator, a thin blood film is made and gas exchange takes place on the surface of the exposed blood film. A third type of blood oxygenator is called a membrane oxygenator. In the membrane oxygenator, the blood is separated from direct contact with the oxygenating gas by a membrane. This membrane must be microporous or semipermeable, that is, the membrane must be capable of permitting carbon dioxide and oxygen to permeate through it while at the same time preventing the blood itself from passing therethrough.

There are two types of membrane blood oxygenators currently available. One type, called the flat plate membrane oxygenator, employs one or more thin, flat sheets of microporous membrane. In its most basic form the flat plate oxygenator has a single sheet of microporous membrane sealed into a housing so as to provide in the housing a first compartment (the "blood compartment") for the flow of blood and a second compartment (the "gas compartment") for the flow of an oxygenating gas. Each of the compartments is fitted with an inlet and an outlet. Blood flows into and out of the blood compartment and the oxygenating gas flows into and out of the gas compartment. Oxygen passes from the oxygenating gas across the membrane into the blood flowing through the blood compartment.

Carbon dioxide passes from the entering blood across the membrane to be entrained in the oxygenating gas. The exiting blood, now reduced in carbon dioxide and enriched in oxygen, is returned to the patient.

The other type of membrane oxygenator, referred to as a hollow fiber oxygenator, is illustrated generally in U.S. Pat. No. 4,239,729 to Hasegawa et al. A hollow fiber oxygenator employs a large plurality (typically, thousands) of microporous or semipermeable hollow fibers disposed within a housing. These hollow fibers are sealed in the end walls of the housing which are then fitted with skirted end caps. One end cap is fitted with an inlet, the other end cap is fitted with an outlet. The peripheral wall of the housing has an inlet located interiorly of one of the end walls and an outlet located interiorly of the other end wall. In the Hasegawa et al. oxygenator, the hollow fibers are aligned in the housing so that their longitudinal axes are generally parallel to the longitudinal axis of the housing. In the Hasegawa et al. device, blood enters through the inlet of one end cap, passes through the lumens of the hollow fibers, and exits through the outlet of the other end cap. The oxygenating gas enters the device through the inlet in the peripheral wall near one end of the device, passes over the outer surfaces of the hollow fibers, and exits the device through the outlet in the peripheral wall near the other end of the device. It will be understood that carbon dioxide diffuses from the blood flowing inside the hollow fibers through the fiber walls into the stream of oxygenating gas. At the same time, oxygen from the oxygenating gas flowing over the outer surfaces of the hollow fibers diffuses through the walls of the hollow fibers into the lumens thereof to oxygenate the blood flowing therethrough.

A hollow fiber oxygenator with an integral heat exchanger has recently become available from the Terumo Corporation under the designation Capiox II. The hollow fibers in the Terumo oxygenator are arranged as the hollow fibers in the Hasegawa et al. device, i.e. the longitudinal axes of the fibers are parallel to the longitudinal axis of the oxygenator housing. In use, blood is passed through the lumens of the hollow fibers while the oxygenating gas is passed over the outer peripheral surfaces of the fibers.

The Terumo oxygenator uses hollow fibers whose inside diameters are about 200 microns and whose wall thickness is about 25 microns. The effective length of the hollow fibers (i.e. the straight line distance between the innermost surfaces of the end walls in which the fibers are imbedded) is about 130–140 mm. depending on the size of the oxygenator. The manufacturer supplies the device in several sizes as measured by the surface area to which the blood to be oxygenated is exposed. Where the blood passes through the lumens of the hollow fibers, as is the case in the Terumo or Hasegawa et al. devices, the surface area, S.A., to which the oxygenating gas is exposed is given by equation (1):

$$S.A. = \pi(I.D.)(\text{length})(n) \tag{1}$$

where (I.D.) is the inside diameter of the fibers, (length) is the effective length of the fibers in the device and (n) is the total number of fibers.

The Terumo oxygenator is currently provided by the manufacturer in four different surface areas, i.e., 1.6 m$^2$, 3.3 m$^2$, 4.3 m$^2$, and 5.4 m$^2$, the largest of these sizes being intended for use on adult patients and the smallest being intended for use on infants. Using these surface areas and the aforementioned inside diameter of the fibers in equation (1), one can calculate that the Terumo oxygenator employs about 62,000, about 53,000, about 20,000 and about 18,000 fibers, respectively, to provide gas exchange surface areas of approximately 5.4 m$^2$, 4.3 m$^2$, 3.3 m$^2$, and 1.6 m$^2$, respectively. Thus, it is seen that even the smallest Terumo oxygenator uses a very large number (about 20,000) of microporous fibers. This large number of fibers makes the oxygenator difficult to assemble and, since the fibers are expensive, adds to the selling price of the final product. Since the Terumo device is designed to have blood flow through the lumens of its hollow fibers, and since those hollow fibers have relatively small inside diameters, there are relatively large blood pressure drops associated with the device. For example, at a surface area of 5.4 m$^2$ and a blood flow of 6 liters per minute, the blood pressure drop is said to be 175 mm. Hg. As another example, at a surface area of 1.6 m$^2$ and a blood flow of 2 liters per minute, the blood pressure drop is said to be about 150 mm. Hg.

In order to facilitate discussion of U.S. Pat. No. 3,442,008 to McLain and other prior art employing spiral winding of fibers on a support core and to more readily understand and appreciate the differences between Applicants' invention and the prior art, it will be helpful to keep in mind the following definitions. "Pitch" is the straight line distance, measured along an imaginary line running parallel to the longitudinal axis of the support core on which a continuous length hollow fiber or fibers are being wound, between any point at which a given hollow fiber crosses that imaginary line and the point at which that same continuous hollow fiber next crosses that imaginary line.

This illustrated in FIG. 12, which shows a six fiber ribbon 100 being spirally wound on a support core. The pitch, P, at which the fibers were wound on the core is the distance measured along imaginary line 91 running parallel to the longitudinal axis of the core, between the point 97 at which fiber 106 first crosses line 91 and the point 98 at which fiber 106 next crosses imaginary line 91.

The term "fiber band width" or "band width" is used to characterize a fiber "ribbon" comprising one or more continuous hollow fibers having a diameter, d. Where a fiber ribbon comprises a number, n, of fibers having a diameter, d, and the fibers of that ribbon, when wound on the support core, are separated by a space, s, the fiber band width, BW, is equal to:

$$\tfrac{1}{2}x + (n)(d) + (n-1)s + \tfrac{1}{2}x,$$

where x=the distance between the last fiber in a ribbon and the first fiber in the next adjacent ribbon on the wound core. This simplifies to BW=(n)(d)+(n−1)(s)+x. Band width can be understood by referring to FIG. 11 of the accompanying drawings which illustrates a fiber ribbon 100 comprising six hollow fibers, designated by numerals 101, 102, 103, 104, 105 and 106. Adjacent fibers in ribbon 100 are separated by a distance, s. At the left side of FIG. 11, there is illustrated a single hollow fiber which has been designated by numeral 96, this hollow fiber being the rightmost fiber in a six fiber ribbon 90 located to the left of fiber ribbon 100 on the wound core. At the right hand side of FIG. 11, there is illustrated a single hollow fiber designated by numeral 111, this hollow fiber being the leftmost fiber in a six fiber ribbon 110 located to the right of fiber ribbon 100 on the wound core. It will be seen that one-half of the spacing, x, between fibers 96 and 101 and one-half of the spacing, x, between fiber 106 and fiber 111 constitute, along with the diameters of the six fibers and the spacings therebetween, the band width, BW, of fiber ribbon 100.

In the case where a fiber ribbon comprising just one continuous hollow fiber is wound on the support core, the band width is equal to the diameter, d, of that fiber plus the distance, x, measured along an imaginary line running parallel to the longitudinal axis of the support core, between adjacent portions of that fiber which contact the surface of the core, said measurement being made after the winding of the core has been completed.

U.S. Pat. No. 3,442,008 to McLain discloses a permeability separatory apparatus comprising selectively permeable hollow fibers which are wound spirally around a cylindrical core through a substantial portion of the length of the core In one embodiment of the separatory apparatus, a region near each end of the core is impregnated with a casting resin so as to form a flange extending annularly and perpendicularly from the core. These flanges are subsequently cut perpendicularly to the axis of the core so as to provide open ends in the fibers at the outer surface of each flange. The core/flange combination is then placed into a generally cylindrical casing and the outer peripheral surface of each flange is sealed in fluid tight relationship to the adjacent inner surface of the casing.

McLain employs one or more continuous hollow fibers and winds the fiber spirally on a cylindrical supporting core. The preferred method of wrapping the fiber on the supporting core consists of revolving the core on its linear axis and then feeding one or more continuous hollow fibers so that the fiber is wound around the core as the core is rotated. A guide positions the fiber on the core as the guide traverses the length of the core, the guide changing direction as it reaches each respective end of the core.

The McLain wrapping method results in a criss-cross pattern of spiral windings of the fiber on the core in which the pitch of the fibers is substantially equal to the fiber band width. As used herein, a "traverse" of the fiber guide is one travel or pass of the fiber guide from its starting point at one end of the rotatable mounting member to the opposite end of the mounting member. In the first traverse of the guide in the McLain method, one or more continuous hollow fibers are laid down on the core. In the second traverse of the guide (which is in the direction opposite to that of the first traverse), fibers are laid down on top of those fibers which were laid down during the first traverse of the guide. The fibers laid down during the second traverse contact the fibers laid down during the first traverse, such contact being at the fiber crossover points, but none of the fibers laid down during the second traverse contact the support core. In the third traverse of the guide (which is in the same direction as the first traverse but in the direction opposite to that of the second traverse), fibers are laid down on top of those fibers laid down during the second traverse of the guide. The fibers laid down during the third traverse of the guide contact the fibers laid down during the second traverse at their mutual crossover points, but none of the fibers laid down during the third traverse contact any of the fibers laid down during the first traverse nor do any of the fibers laid down during the third traverse contact the surface of the support core on which the fibers are being wound. In the fourth traverse of the guide (which is in the same direction as that of the second traverse and in the direction opposite to that of the first and third traverses), fibers are laid down on top of those fibers which were laid down during the third traverse of the guide. The fibers laid down during the fourth traverse of the guide contact the fibers which were laid down during the third traverse of the guide at their mutual crossover points, but none of the fibers laid down during the fourth traverse contact the fibers laid down during the second traverse of the fibers laid down during the first traverse nor do they contact the surface of the support core. If a transverse cross-section be taken through McLain's fiber wound core after two traverses the guide, the thickness of the fiber wrapping applied to the core is equal to two fibers diameters. After the third traverse of the guide in McLain, the thickness of the fiber wrapping is three fibers diameters. After the fourth traverse of the guide in McLain, the thickness of the fiber wrapping is four fiber diameters.

The foregoing can be stated more generally as follows: where the guide in McLain has gone through n traverses ($2^n$) traverses in each direction), the fibers laid down during the $n^{th}$ traverse of the guide contact, at their mutual crossover points, the fibers which were laid down during the $N-1)^{th}$ traverse. The fibers laid down during the $n^{th}$ traverse do not contact fibers laid down during the $(n-2)^{th}$ or any earlier traverse nor do the fibers laid down during the $n^{th}$ traverse of the guide contact the support core. Where the fiber guide in McLain has made n traverses, the thickness of the fiber wrapping applied to the core is substantially equivalent to n fiber diameters.

It will be recognized that where McLain wraps a single continuous hollow fiber, the fiber diameter, d, plus the spacing between adjacent fibers in contact with the support core after the winding process has been completed is equivalent to the pitch, P, at which the single continuous hollow fiber was wound on the support core. Unless otherwise indicated or unless the context requires otherwise, distances referred to in this patent application are distances which have been determined with respect to an imaginary straight line running parallel to the longitudinal axis of the support core. Where McLain wraps a "ribbon" of two or more continuous hollow fibers, then the pitch is equal to the band width.

A spirally wound hollow fiber oxygenator device has recently been brought to market by C. R. Bard. Upon examination of this device, it appears that a "ribbon" of about 100 or so continuous hollow fibers has been spirally wrapped on a support core and it appears also that the winding process was carried out using the McLain apparatus and procedure just discussed. In the Bard device, the pitch at which the ribbon of fibers is wound onto the support core is equal to the ribbon band width as was the case with the McLain device previously discussed. None of the fibers in the Bard device's second layer of fibers (i.e., the fibers laid down during the second traverse of the guide contacts the support core. None of the fibers in the third layer (i.e. the fibers laid down during the third traverse of the guide) contact the fibers of the first layer nor do they contact the support core itself. Fibers in the fourth layer of fibers (i.e., the fibers laid down during the fourth traverse of the guide) do not contact fibers in the second layer or the first layer nor do they contact the support core. In the Bard device, the thickness of the final fiber bundle is equal to n fiber diameters, where n=the number of traverses made by the fiber guide during the Bard winding operation. In short, the only difference between the fiber wound support core specifically illustrated in the McLain patent (FIG. 5) and the fiber wound support core employed in the Bard device is that the former was made by winding a single continuous hollow fiber while the latter was made by winding a ribbon of 100 or so continuous hollow fibers.

SUMMARY OF THE INVENTION

It has now been discovered that a greatly improved spirally wound hollow fiber mass transfer device can be made by winding one or more continuous microporous hollow fibers on a core such that the ratio of the pitch at which the fiber or fibers are wound on the core to the fiber band width is greater than unity. Preferably, the ratio of pitch to fiber band width is at least about 2. Excellent blood oxygenation has been obtained, for example, at a pitch to fiber band ratio of about 9. At any given pitch to fiber band width ratio, best mass transfer efficiency is obtained when, after the core has been completely wound with fiber, the spacing, s, between adjacent fibers in a ribbon is equal to the distance, x, between the last fiber in a fiber ribbon and the first fiber in the next adjacent fiber ribbon.

The mass transfer device may be provided with an integral heat exchanger. Thus, for example, where the mass transfer device is to be used as a blood oxygenator, the temperature of the blood may be raised or lowered as desired during a surgical procedure.

The mass transfer device of the present invention will be described as a blood oxygenator which is used to extracorporeally oxygenate a patient's blood during, for example, the course of open heart surgery. It will be recognized by those skilled in the art that the mass transfer device can be used for other purposes.

Blood oxygenators made in accordance with the teachings of the present invention employ much less hollow fiber surface area than prior art devices as a result of which there is less foreign body surface area (i.e. the surfaces of the hollow fibers) which the blood may contact.

Despite the fact that there is less hollow fiber surface area compared to prior art devices, the mass transfer efficiency of an oxygenator made in accordance with the present invention is equal to or better than known prior art hollow fiber oxygenators. The oxygenator of the present invention has a greatly reduced priming volume and is much more compact than existing devices.

BRIEF DESCRIPTION OF THE DRAWINGS

FIG. 4 is an exploded view of the oxygenator of FIG. 1 and showing the top header, the outer casing, inner support core, and the bottom header with optional heat exchanger;

FIG. 5 is a bottom plan view, showing the inner surfaces, of the top header of the oxygenator;

FIG. 6 is a section taken along line 6—6 of FIG. 5;

FIG. 7 is a top perspective of the outer casing of the oxygenator;

FIG. 8 is a "front" perspective of the outer casing as viewed perpendicularly to line 8—8 of FIG. 7;

FIG. 9 is a "side" perspective of the outer casing viewed perpendicularly to line 9—9 of FIG. 8;

FIG. 12 is a view of the support core with its core extenders in place showing the location of a ribbon of six hollow fibers on the core at an early stage of the fiber winding process;

FIG. 13 is a greatly enlarged view of the dot-and-dashed portion of FIG. 12;

FIG. 14 is a sectional view taken along 14—14 of FIG. 13;

FIG. 15A is a view similar to FIG. 12 showing the placement of fibers on the support core at a later stage of the winding process;

FIG. 16A is a view similar to that of FIGS. 12 and 15A showing the placement of fibers at a still later stage of the winding process;

FIG. 17 is a very greatly enlarged view showing the path of a first fluid through the interiors of the hollow fibers and the highly random path which a second fluid might take as it flows through the fiber bundle during operation of the device.

DETAILED DESCRIPTION OF THE INVENTION

Figure 1:
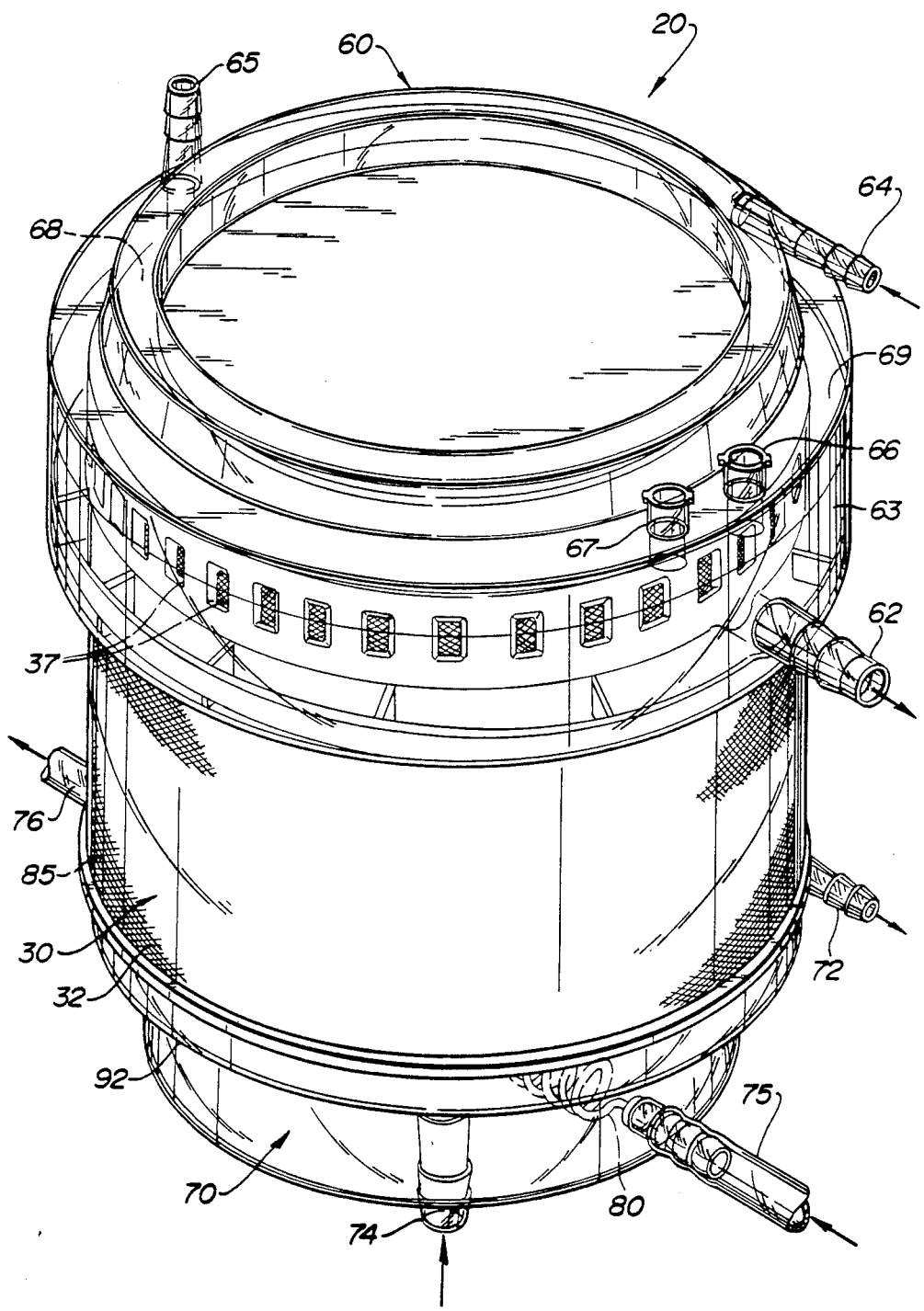
FIG. 1 is a perspective view of a spirally wound hollow fiber oxygenator in accordance with the present invention.
Figure 2:
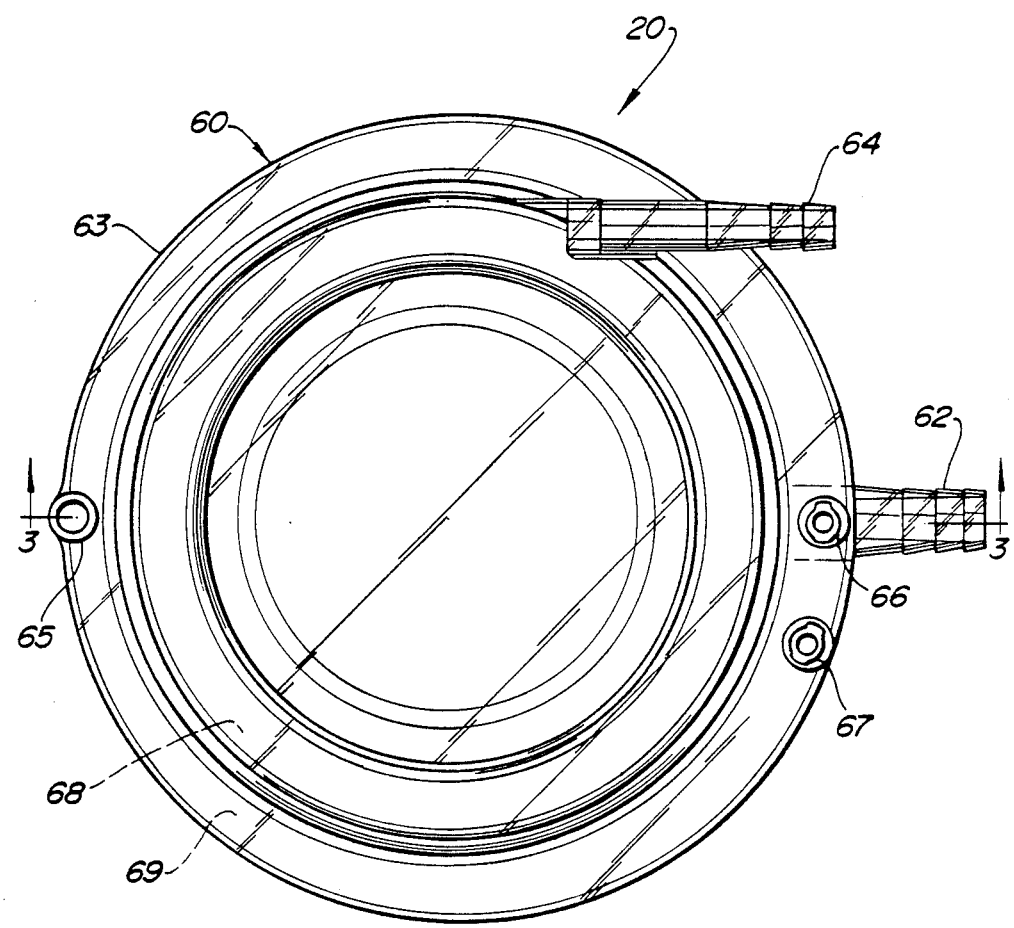
FIG. 2 is a top plan view of the oxygenator of FIG. 1.
Figure 3:
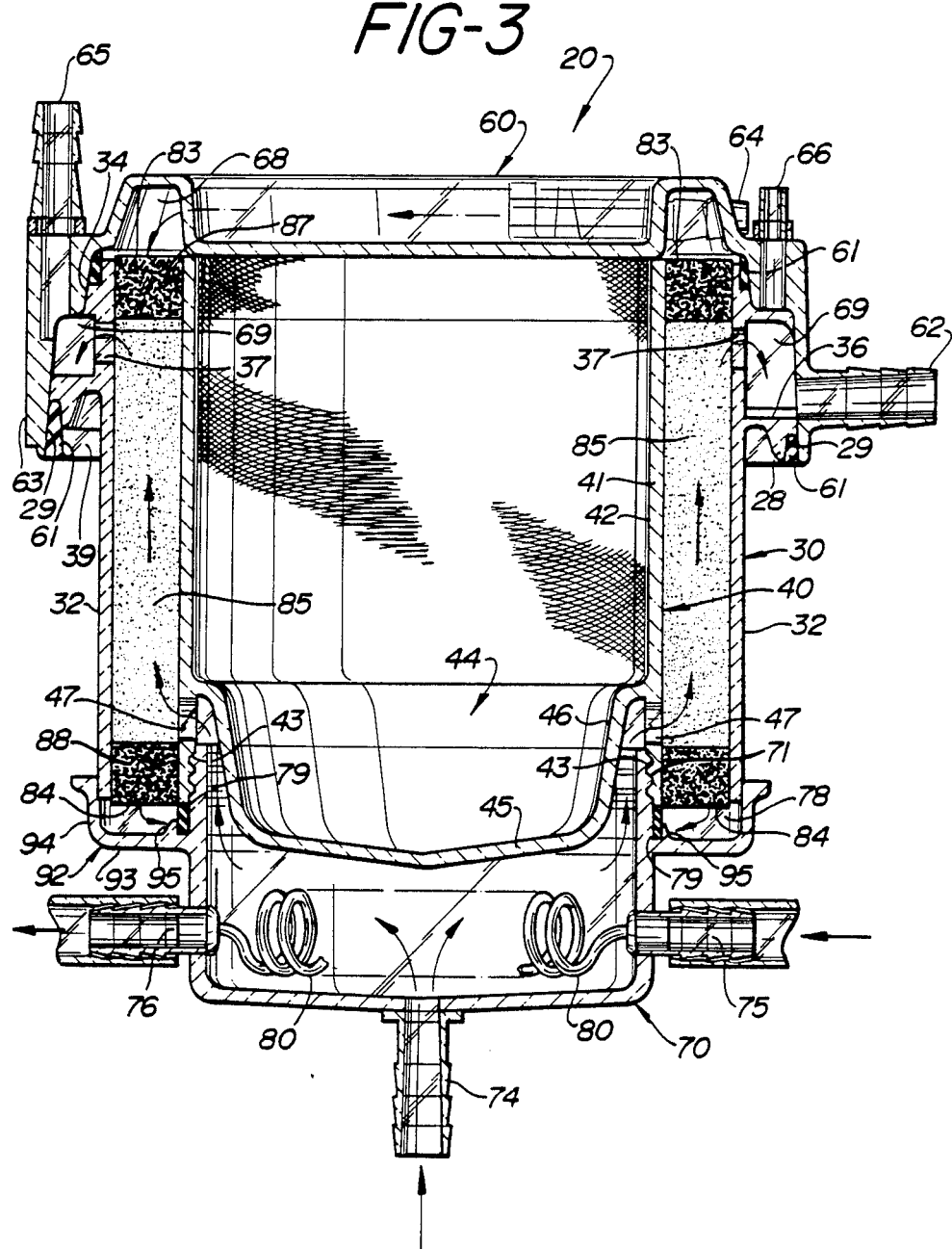
FIG. 3 is a vertical cross-section of the oxygenator of FIG. 1.

Referring now to the drawings, and especially to FIGS. 1–10 thereof, a blood oxygenator 20 in accordance with the present invention comprises a cylindrical outer casing 30, a cylindrical inner support core 40 on which are wound, in the manner to be explained hereinafter, a ribbon of six continuous semipermeable hollow fibers, a top end cap or header 60 and a bottom end cap or header 70. The blood oxygenator may optionally include a heat exchanger 80, which as shown in FIG. 3 may be associated with the bottom header which includes an inlet 74 for the introduction into the oxygenator of blood taken from a patient.

Outer casing 30 has a cylindrical peripheral wall 32 and, prior to assembly of the oxygenator, is open at both its ends. The exterior surface of the outer casing comprises a first annular flange 34 which is spaced a slight distance downwardly from the upper end of the casing and a second flange 36 which is spaced a distance downwardly from first flange 34. The portion of peripheral wall 32 lying between the first and second annular flanges is provided with a series of generally rectangular openings 37. The function of openings 37 will be explained hereinafter.

Inner support core 40 comprises a cylindrical peripheral wall 41 which includes an interiorly threaded portion 43 adjacent its bottom end. Support core 40, which prior to assembly of the oxygenator is open at its top end, includes a dish portion 44 which serves to close off its bottom end. Dish portion 44 includes a bottom portion 45 and an angled wall portion 46. As can be seen in FIG. 3 and also in FIG. 10, angled wall portion 46 of dish portion 44 is sealed in fluid tight relationship to the inner surface 42 of peripheral wall 41 at a point located upwardly of threaded portion 43. Peripheral wall 41 is provided with a series of apertures 47 between threaded portion 43 and the point at which angled wall portion 46 is sealed to inner surface 42 of wall 41. The purpose of these apertures will be explained hereinafter.

Top header 60 has an outlet 62 through which, as will be seen hereinafter, blood is removed from the oxygenator after it has been oxygenated. Top header 60 also includes an inlet 64 for the introduction of an oxygenating gas into the lumens of the spirally wound hollow fibers. Top header 60 also includes a recirculation port 65, an arterial blood sampling port 66, and a temperature probe connector 67.

Bottom header 70 has an outlet 72 through which the oxygenating gas is removed from the oxygenator after it has passed through the lumens of the hollow fibers. Bottom header 70 also has a blood inlet 74, an inlet 75 for introducing a heat exchange fluid into heat exchanger 80, and an outlet 76 for withdrawing heat exchange fluid from the heat exchanger.

An annular bundle 85 of spirally wound microporous hollow fibers is located in the space defined by the outer wall of inner support core 40 and the inner wall of outer casing 30. This fiber bundle is embedded in a solidified potting composition at its top and bottom ends. As will be seen hereinafter, the fiber lumens communicate with the outer surface of the upper and lower potted portions 87 and 88, respectively, so that oxygenating gas introduced via gas inlet 64 flows into gas passage 68 in top header 60, then into the open ends of the hollow fibers at the upper surface of the upper potted portion 87, then through the lumens of the hollow fiber, then through the open ends of the hollow fibers at the lower surface of the potted portion 88, then into gas passage 78 in header 70, and finally out of the oxygenator via gas outlet 72.

In use, blood to be oxygenated is introduced through blood inlet 74, passes over heat exchanger 80, is directed by the outer surface of dish 44 toward and through openings 47 in support core 40. The blood then flows upwardly, i.e., axially of the oxygenator, over the outer surfaces of the semipermeable hollow fibers. Upon reaching the lower surface of potted portion 87, the blood, now oxygenated, flow through openings 37 in outer casing 30 into arterial blood passage 69 which is defined by the inner surface of skirt portion 63, the upper surface of flange 36, a portion of the lower surface of annular flange 34 and that portion of wall 32 lying between flanges 34 and 36. The blood then exits the oxygenator through blood outlet 62. The arrows in FIG. 17 depict the tortuous path taken by the blood in flowing through the spirally wound fiber bundle. It will be seen that the general flow pattern of the blood is upwardly and axially through the fiber bundle, i.e., in a direction which in general is parallel to the axis of the fiber bundle 85. This flow pattern, in which blood travels over and under the hollow fibers, gives good blood phase mixing which in turn gives excellent gas transfer. The oxygenating gas flows through gas inlet 64 into gas passageway 68, thence into the open ends of the fibers at the outer surface of potted end portion 87, through the fiber lumens, out of the fiber end at the outer surface of pottend end portion 88, into gas passage 78, and finally out of the oxygenator through gas outlet 72 in bottom header 70.

Figure 10:
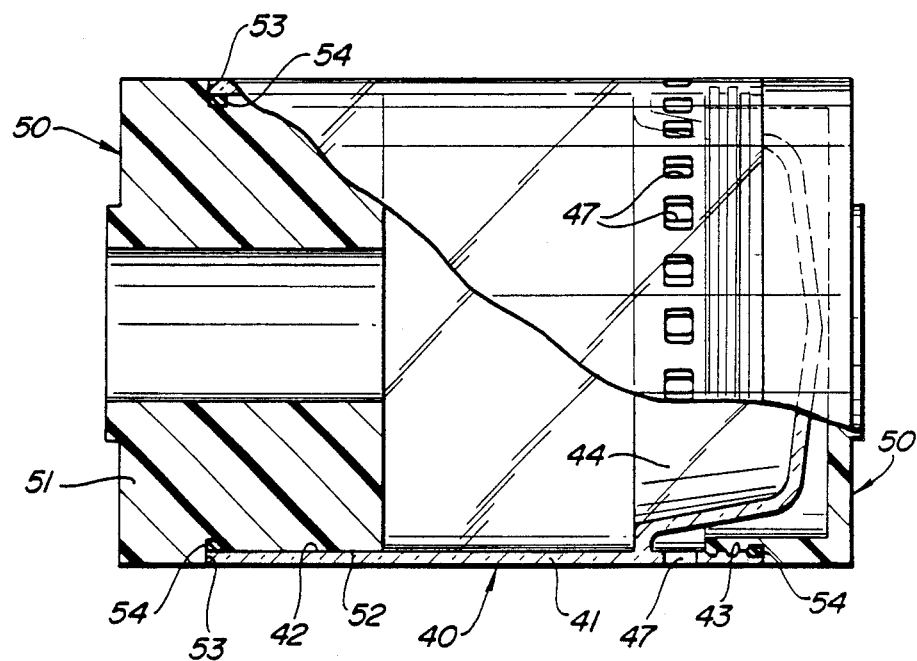
FIG. 10 is a perspective, with parts in cross-section, of the inner core and core extenders prior to start of the fiber winding operation.
Figure 11:
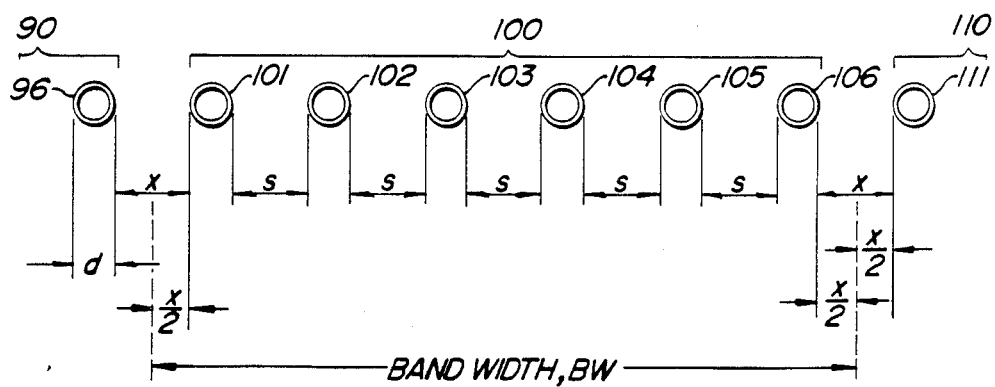
FIG. 11 is a highly magnified view of a ribbon of six hollow fibers and their spacing as they are about to be wound on the inner support core.

The procedure for spirally winding semipermeable hollow fiber on a supporting core in accordance with the present invention will now be described. Referring to FIG. 10, a cylindrical support core 40 is fitted at each of its ends with a cylindrical core extender 50. Core 40 is preferably hollow and has a wall thickness of about 0.125 inch (0.32 centimeters). In an illustrative embodiment, the support core is conveniently about 4.5 inches (11.4 centimeters) long and has an outside diameter of about 4 inches (10.2 centimeters). Each core extender 50 comprises a main portion 51 joined to a reduced diameter portion 52 at a shoulder 53. Reduced diameter portion 52 is sized so that its outer surface may be friction fitted with the inner surface 42 of core 450. The outside diameter of core extender 50 corresponds substantially to that of core 40 so that when the extenders are inserted into the ends of the core with shoulders 53 abutting the ends of the support core, there is provided an extended core having a substantially uniform outside diameter. Gaskets 54 are placed around reduced diameter portions 52 near shoulders 53.

The hollow fiber winding process may be conveniently performed on an apparatus of the type illustrated schematically in FIG. 12. The fiber winding apparatus comprises a revolving mounting member 122 and a fiber guide 124 which travels reciprocally as illustrated by double-headed arrow "A" in FIG. 12, along a line parallel to the axis of rotation of the mounting member. The fiber guide contains a number of upstanding guide pins, not illustrated in FIG. 12, through which the fibers are threaded as they enter the guide from a supply container. A winding apparatus sold commercially by Lesona Corporation under the name Precision Wind Take-Up Machine, Model No. 959 (or equivalent) is suitable for wrapping a continuous hollow fiber (or a number of such hollow fibers ) on the extended support core.

The extended core just described is spirally wound with hollow fibers in the following manner. The extended inner support core is mounted on mounting member 122 of the winding apparatus. Guide 124 is then positioned at the left hand side (as viewed in FIG. 12) of the extended core. A ribbon of six continuous semipermeable hollow fiber is taken from a supply container, threaded over an idler roll, under a "dancing" roll, and then through the guide pins of fiber guide 124. Seven such guide pins are used, one continuous hollow fiber being placed between two adjacent pins in order to separate the fibers as they leave the supply continer. The leading end of the fiber ribbon is tied into a small knot which is then affixed, as by taping, to the outer surface of the core extended at the far left end of the extended core. Rotation of mounting member 122 of the winding apparatus is begun in the direction indicated by arrow B in FIG. 12. Guide 124 is geared to mounting member 122 and automatically travels axially of the extended core as mounting member 122 rotates. It will be recognized by those skilled in the art that guide 124 travels axially a fixed distance for each revolution of mounting member 122 and that this fixed distance corresponds exactly to the pitch at which the fibers are wound on the extended support core. Thus, "pitch" may alternatively be defined as the linear distance traveled by guide 124 during one revolution of mounting member 122 of the winding apparatus.

Guide 124 travels from the first end (left hand side of FIG. 12) of the extended core to the second end (right hand side of FIG. 12) where, after a brief dwell time, the guide reverses direction and travels back to its starting position. After a brief dwell time at that point, the guide begins its travel cycle anew. This reciprocal travel for guide 124 and the concurrent rotation of mounting member 122 on which the extended support core has been mounted is continued until a fiber bundle of desired diameter has been wound onto the extended core.

FIG. 13 is a greatly enlarged view of the dot-and-dash enclosed portion of FIG. 12 which shows the position of the six fiber ribbon 100 after the fiber guide 124 left its starting position at the left hand side of FIG. 12, traveled to the right hand side of FIG. 12, reversed directin, and traveled leftward to its position illustrated at the top of FIG. 12. In the left-to-right travel of guide 124, the fiber ribbon was wound spirally around the extended support core at pitch, P, and the individual fibers 101–106 in the ribbon were laid down in contact with the outer surfaces of support core 40 and core extenders 50. In the subsequent second traverse (right-to-left in FIG. 12) of guide 124, fiber ribbon 100 continues to be spirally wound onto the extended core. It will be seen that portions of the six fibers (labeled 101', 102', 103', 104', 105', and 106') laid down during the second traverse of the fiber guide contact fibers 101–106 at certain crossover points. Except for these crossover points at which there is fiber-to-fiber contact with fibers laid down during the first traverse of guide 124, the fibers laid down during the second traverse of the fiber guide come into direct contact with the outer surface of the extended core.

FIG. 15A shows the appearance of the fibers on the extended core after the guide 124 has completed 7 traverses in the left-to-right direction, 7 traverses in the right-to-left direction, and is approaching the end of its 8th traverse in the left to right direction. It will be observed that despite the 14+ total traverses of the fiber guide, there still remain certain areas of the support core 40 which have not yet been wound and covered with the fiber ribbon.

Figure 15B:
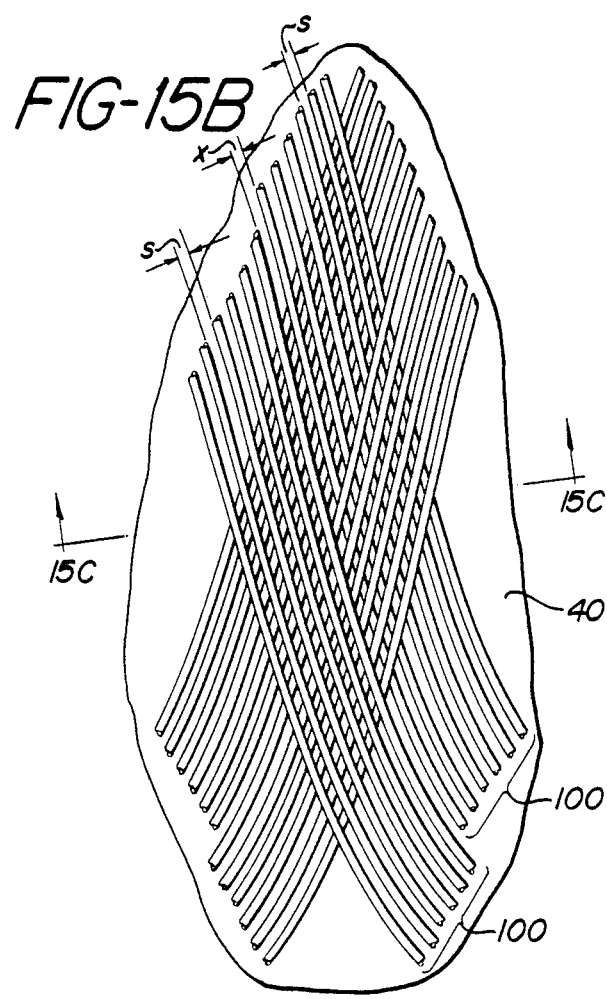
FIG. 15B is a greatly magnified view of the circled portion of FIG. 15A.
Figure 15C:
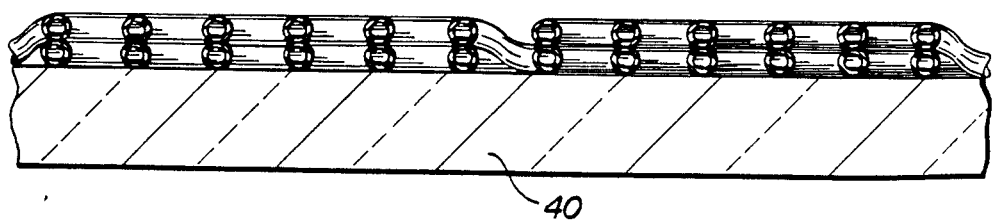
FIG. 15C is a cross-section taken along line 15C—15C of FIG. 15B.

FIG. 15B is a greatly magnified view of the dot-and-dash enclosed portion of FIG. 15A. Reference to FIG. 15B and to FIG. 15C clearly shows that even after nearly 15 total traverses of the fiber guide there is only one thickness of fiber (equal to on fiber diameter) on some portions of the extended support core and at most there are two thicknesses of fiber (equal to two fiber diameters). Areas where fiber coverage is just one fiber diameter thick are illustrated at the upper right hand and upper left hand regions of FIG. 15B. Area where fiber coverage is just two fiber diameters thick are shown in the lower central region of FIG. 25B and in FIG. 15C.

FIG. 16A shows the appearance of the fibers on the extended core at a stage of winding later than that shown in FIG. 15A. In FIG. 16A, the fiber guide has completed 9 traverses in the first direction (left-to-right in FIG 12) and 8 traverses in the second direction (right-to-left in FIG. 12) and is about to complete its 9th traverse in the second direction. It will be seen in FIG. 16A that, except for the spacing, s, between adjacent fibers of the fiber ribbon 100 and the distance, x, between adjacent ribbons, there are no open areas on the surface of the extended core which are uncovered by fiber.

In the winding procedure being discussed, the extended core is covered, except for the spacing, s, between adjacent fibers and the distance, x, between the sixth fiber of one ribbon and the first fiber of the next adjacent ribbon, when the fiber guide has traveled a total of eighteen traverses, i.e. nine traverses in each direction. Fibers 101-106 of the fiber ribbon laid down during the nineteenth traverse of the fiber guide will be in radial registry with fibers 101-106 laid down during the very first traverse of the fiber guide and fibers 101-106 laid down during the twentieth traverse of the fiber guide will be in radial registry with fibers 101-106 laid down during the second traverse of the fiber guide. Stated more generally, in the particular embodiment under discussion, fibers 101-106 laid down during the $n^{th}$ traverse of the fiber guide will be in registry with fibers 101-106 laid down during the $(n-18)^{th}$, $(n-36)^{th}$, $(n-54)^{th}$ traverse of the fiber guide. For example, fibers 101-106 laid down during the $55^{th}$ traverse will be in radial registry with fibers 101-106 laid down during the $37^{th}$, $19^{th}$ and $1^{st}$ traverses of the fiber guide.

It will also be understood at the completion of the $36^{th}$ traverse of the fiber guide, the thickness of the fiber bundle on the extended core will be equal to four fiber diameters; at the end of the $54^{th}$ traverse, the thickness of the fiber bundle will be equal to six fiber diameters; at the completion of the $72^{nd}$ traverse, the thickness of the fiber bundle will be eight fiber diameters, etc.

It is preferred in carrying out the spiral winding process of the present invention that the spacing, s, between adjacent fibers in a ribbon be the same and that the distance, x, between adjacent fiber ribbons be equal to s.

However, this is not mandatory. It is possible to obtain the benefits of the present invention in cases where the distance, x, between adjacent fiber ribbons is not equal to the spacing, s, between adjacent fibers in the fiber ribbon. Where, for example, x is larger than s, it is believed that other factors being equal, some reduction in mass transfer efficiency may be observed. Also it is not mandatory that the spacing, s, between adjacent fibers in a fiber ribbon be the same. It is possible to vary the spacing, s, between adjacent fibers and still obtain many benefits, including greatly increased mass transfer efficiency, over the structures of the prior art. The critical feature of the present invention, as has been indicated earlier herein, is that the ratio of the pitch at which the fiber ribbon is wound onto the core to the fiber band width must be greater than unity and preferably is at least 2.

Figure 18:
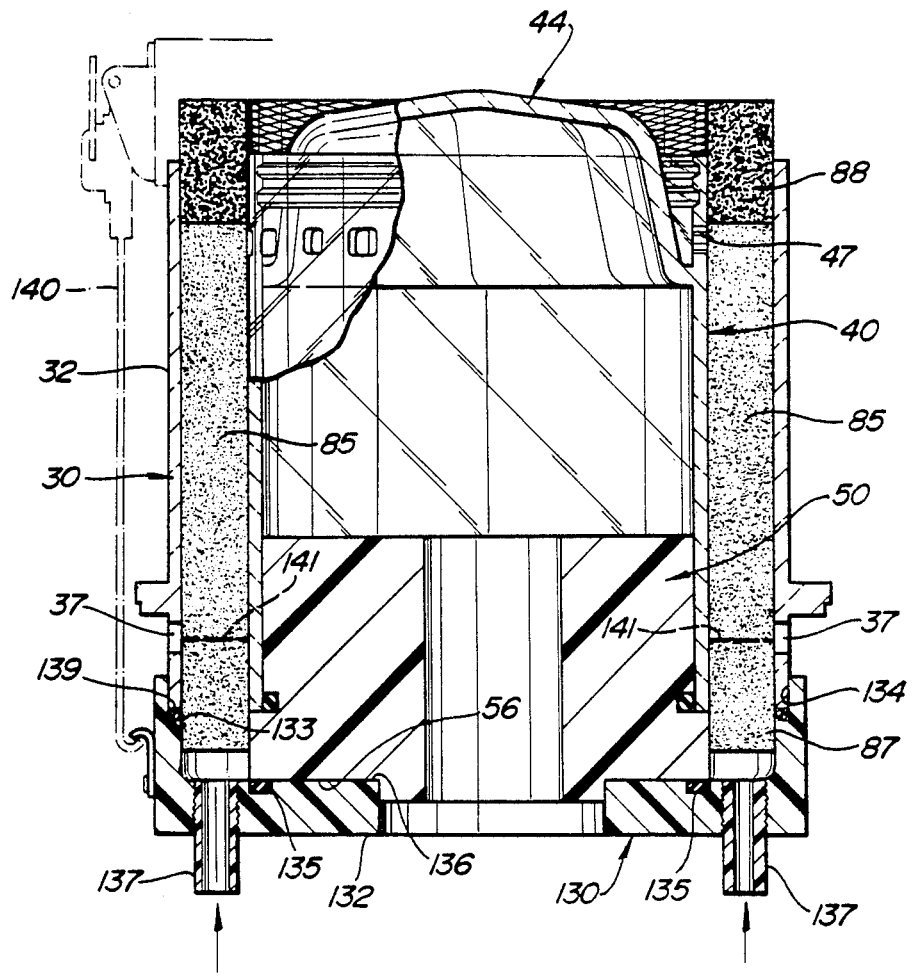
FIG. 18 is a sectional view, with parts cut away and other parts in phantom, showing the inner core (with core extenders at each end and fibers wrapped around the extended core) disposed in an outer casing at an intermediate stage of the end wall potting operation.

After the desired amount of fiber has been spirally wound onto the extended core in the manner just explained, the extended core with the fiber bundle 85 wound thereon is removed from mounting member 122 of the winding apparatus. The fiber bundle/core combination is then inserted into outer casing 30, the fiber bundle having been sized during the winding procedure so that its outside diameter is about equal to the inside diameter of the outer casing. It is necessary now to apply a liquid form casting resin to the end portions of the fiber bundle, and to allow that resin to harden or cure so as to seal the fibers near the ends of the fiber bundle to each other, to the adjacent outer surface of inner support core 40, and to the adjacent inner surface of outer casing 30. The process, referred to in the art as a "fiber potting process", is carried out with the aid of a potting cap. The bottom portion of FIG. 18 shows potting cap 130 in place over one end of the extended support core/fiber bundle/outer casing combination. Potting cap 130 comprises a circular end portion 132 and a skirt portion 134 depending therefrom. Skirt portion 134 has a shoulder 133 whose width is substantially equal to the thickness of peripheral wall 32 of outer casing 30. When the potting cap is in place, a gasket 139 is placed against shoulder 133 to form a fluid tight seal with the end edge of outer casing 30. Potting cap 130 includes an O-ring 135 placed in a circular groove cut into the inner surface 136 of end portion 132. The groove for the O-ring is located such that when the potting cap is in position, O-ring 135 contacts the periphery of the end face 56 of core extender 50. Potting cap 130 includes two inlets (one inlet would be sufficient) through which the potting resin is applied to the end of the fiber bundle. The potting cap may be secured in place by a friction fit where the inner wall of its skirt portion 134 contacts the outer surface of outer casing 30. Alternatively, a clamping device 140 such as that illustrated in phantom at the left side of FIG. 18 may be used for this purpose.

The liquid potting compound is conveniently applied to the end portions 87, 88 of the fiber bundle 85 as follows. The support core/fiber bundle/outer casing combination, with potting cap 130 in place, is oriented in the direction in which the reader views FIG. 18. A quantity of liquid potting resin is injected, e.g. by using a syringe, into the inlets 137 of potting cap 130. Sufficient resin is injected so that it rises to the level indicated by dashed line 141 and the inlets are closed. Care is taken to make sure the liquid resin rises no higher than the level indicated by line 141 so as to preclude its running through openings 37 in outer casing 30. When the resin level reaches dashed line 141, it is left to cure or harden to its fully solid state. After the first end of the support core/fiber bundle/outer casing combination has been potted as just described and the potting resin has fully hardened, potting cap 130 is removed and the other end is potted in the same manner. The potting cap is removed from the second end and then both core extenders 50 are removed. This leaves the potted fiber bundle disposed between the outer surface of the inner support core 40 and the inner surface of outer casing 30. The fibers at the end of the fiber bundle are embedded in the cured potting composition. One region of each potted end portion of the fiber bundle is sealed to the outer surface of support core 40 and to the inner surface of outer casing 30. A second region of each potted end portion of the fiber bundle extends beyond the aligned end edges of support core 40 and outer casing 30. Each extending potted end portion is then cut transversely of the longitudinal axis of the support core so that the freshly cut surfaces of the potted portions are flush with the ends of the support core and the outer casing. It will be recognized that the transverse cutting of the potted end portions 87, 88 of the spirally wound fiber bundle provides open ends in the fibers at the outermost cut surface 83 of potted end portion 87 and at the outermost cut surface 84 of potted end portion 88. This provides a continuous path for the flow of a fluid through the lumens of the semipermeable hollow fibers from the cut outer face of one potted end portion of the fiber bundle to the cut outer face of the other potted end portion of the fiber bundle.

After the potting and transverse cutting operations have been completed, gasket 61 is placed around the upper part of first annular flange 34. Top header 60, which has support fins 39 supporting annular flange 36, is then put into position over the open end of support core 40 (see top portion of FIG. 3). Header 60 has a skirt portion 63 whose inner surface, when the header is in position, abuts the outer surface of second annular flange 36. The abutting surfaces may be sealed, e.g. by solvent welling or another suitable method. It is advisable to place a sealing compound 61 in the inverted U-shaped region 29 formed by the lowermost portion of skirt 63 and the projecting tip 28 of annular flange 36.

Bottom header 70 includes an L-shaped flange 92 having a bottom portion 93, an outer side wall 94, and a slanted inner wall 95. A groove is cut into slanted inner side wall 95 to accept a gasket 79. This gasket is put into place and the bottom header 70, which carries outer threads 71, is screwed onto the inner threaded portion 43 of the inner support core. It will be seen that gas passage 78 is defined by the outermost surface of potted end portion 88, gasket 79 and the inner surface of bottom wall 93, side wall 94, and slanted wall 95.

EXAMPLE 1

A spirally wound, axial flow hollow fiber blood oxygenator was made according to the method described herein. The inner support core was wound with a fiber ribbon containing 6 microporous polypropylene fibers having an outside diameter of about 470 microns, a wall thickness of about 35 microns, and a mean pore size of about 0.02 microns. The spacing, s, between adjacent fibers in the fiber ribbon was about 0.039 inch (0.1 cm.). The fibers were wound at a pitch of 3.1 inches (7.9 cm) while maintaining a distance, x, of about 0.039 inch (0.1 cm) between adjacent fiber ribbons on the support core. The fiber band width was 0.346 inch (0.88 cm) and the ratio of pitch to fiber band width was 9. The wound fiber bundle was about 0.562 inches (1.43 cm.) thick and provided a gas exchange surface area of about 2.0 square meters. After assembly into an oxygenator of the type shown and described in the specification and drawings, the oxygenator was tested using bovine blood.

When tested in accordance with AAMI OXY-D(2/80)R Standard For Blood/Gas Exchange Devices—Oxygenating (Draft), this oxygenator had a oxygen transfer of about 320 ml/min. at 6 liters/minute blood flow, a carbon dioxide transfer of about 320 ml/min. at 6 liters/minute blood flow and a gas to blood flow ratio of 2. The oxygenator had a priming volume of 480 ml and a blood phase pressure drop of 75 mmHg.

EXAMPLE 2

Two spirally wound, axial flow hollow fiber blood oxygenators were made according to the method described herein. Two inner support cores, each about 4.5 inches (11.43 cm.) long and about 4.0 inches (10.16 cm.) in outside diameter, were wound with a fiber ribbon containing three (3) continuous length, semipermeable hollow polypropylene fibers having an outside diameter of about 470 microns, a wall thickness of about 35 microns, and a mean pore size of about 0.03 microns. The spacing, s, between adjacent fibers in the fiber ribbon was about 0.027 inch (0.069 cm.). The fibers were wound at a pitch of 3.682 inches (9.352 cm.) while maintaining a distance, x, of about 0.027 inch (0.069 cm.) between adjacent fiber ribbons on the support core. The fiber band width was 0.136 inch (0.345 cm.) and the ratio of pitch to fiber band width was about 27.1. The wound fiber bundles were about 0.562 inches (1.43 cm.) thick and provided, in the assembled oxygenators, an average effective gas exchange surface area of about 1.99 square meters.

Each support core with the semipermeable hollow fiber wound thereon was assembled into an oxygenator of the type shown and described in the specification and drawings. The two resulting oxygenators were then tested, using bovine blood, in accordance with the AAMI Standard mentioned in Example 1. The average oxygen transfer was determined to be 352 ml/minute at a blood flow of 6 liters/minute; the average oxygen transfer efficiency was therefore 176.9 ml/minute/meter$^2$ (the average oxygen transfer of 352 ml/minute ÷ average effective gas transfer area of 1.99 meters$^2$). The average carbon dioxide transfer was determined to be 357 ml/minute at a blood flow of 6 liters/minute and a gas to blood flow ratio of 2; the average carbon dioxide transfer efficiency was therefore 179.4 ml/minute/meter$^2$ (the average carbon dioxide transfer of 357 ml/minute ÷ the average effective gas transfer area of 1.99 meters$^2$). The average blood phase pressure drop of the two oxygenators during testing was determined to be 91 mmHg at 6 liters/minute blood flow. In this Example 2, the extended inner support core was covered, except for the spacing, s, between adjacent fibers in the fiber ribbon and the distance, x, between the third (3rd) fiber of one ribbon and the first fiber of the next adjacent ribbon, when the fiber guide on the winding apparatus had traveled a total of fifty-four (54) traverses, i.e. twenty-seven traverses in each direction. The three fibers of the fiber ribbon laid down during the fifty-fifth (55th) traverse of the fiber guide were in radial registry with the three fibers laid down during the very first traverse of the fiber guide, the three fibers of the fiber ribbon laid down during the one hundred ninth (109th) traverse were in radial registry with the three fibers of the fiber ribbon laid down during the first (1st) and fifty-fifth (55th) traverses, etc.

At the completion of the fifty-fourth (54th) traverse of the fiber guide, the thickness of the fiber bundle on the extended core was equal to two fiber diameters; at the end of the one hundred eighth (108th) traverse, the thickness of the fiber bundle was four fiber diameters high; at the end of the one hundred sixty-second (162nd) traverse, the thickness of the fiber bundle was six fiber diameters high; at the end of the two hundred sixteenth (216th) traverse, the thickness of the fiber bundle was eight diameters high, etc.

EXAMPLE 3

Two spirally wound, axial flow hollow fiber blood oxygenators were made according to the method described herein. The support cores had the same length and outside diameter as the support cores used in Example 2. The semipermeable hollow fiber had the same outside diameter, wall thickness and mean pore size as the semipermeable hollow fiber used in Example 2. Each inner support core was spirally wound with a fiber ribbon containing nine (9) hollow fibers. The spacing, s, between adjacent fibers in the fiber ribbon was about 0.0257 inch (0.04 cm.). The fibers were wound at a pitch of about 4.307 inches (10.94 cm.) while maintaining a distance, x, of about 0.0157 inch (0.04 cm.) between adjacent fiber ribbons on the core. The fiber band width was 0.308 inch (0.78 cm.) and the ratio of pitch to fiber band width was about 14. The wound fiber bundles were about 0.562 inches (1.43 cm.) thick and provided, in the assembled oxygenators, an average effective gas exchange surface area of about 2.1 square meters.

Each support core with the semipermeable hollow fiber wound thereon was assembled into an oxygenator of the type shown and described in the specification and drawings. The two resulting oxygenators were then tested, using bovine blood, in accordance with the AAMI Standard mentioned in Example. The average oxygen transfer was determined to be 369 ml/minute at a blood flow of 6 liters/minute; the average oxygen transfer efficiency was therefore 175.7 ml/minute/meter$^2$ (the average oxygen transfer of 369 ml/minute $\div$ the average effective gas transfer area of 2.1 meters$^2$). The average carbon dioxide transfer was determined to be 386 ml/minute at a blood flow of 6 liters/minute and a gas to blood flow ratio of 2; the average carbon dioxide transfer efficiency was therefore 183.8 ml/minute/meter$^2$ (the average carbon dioxide transfer of 386 ml/minute $\div$ the average effective gas transfer area of 2.1 meters$^2$). The average blood phase pressure drop of the two oxygenators during testing was determined to be 115 mmHg at 6 liters/minute blood flow. In this Example 3, the extended inner support core was covered, except for the spacing, s, between adjacent fibers in the fiber ribbon and the distance, x, between the ninth (9th) fiber of one ribbon and the first fiber of the next adjacent ribbon, when the fiber guide on the winding apparatus had traveled a total of twenty-eight (28) traverses, i.e. fourteen traverses in each direction. The nine fibers of the fiber ribbon laid down during the twenty-ninth (29th) traverse of the fiber guide were in radial registry with the nine fibers laid down during the very first traverse of the fiber guide, the nine fibers of the fiber ribbon laid down during the fifty-seventh (57th) traverse were in radial registry with the nine fibers of the fiber ribbon laid down during the first (1st) and twenty-ninth (29th) traverses, etc.

At the completion of the twenty-eighth (28th) traverse of the fiber guide, the thickness of the fiber bundle on the extended core was equal to two fiber diameters; at the end of the fifty-sixth (56th) traverse, the thickness of the fiber bundle was four fiber diameters high; at the end of the eighty-fourth (84th) traverse, the thickness of the fiber bundle was six fiber diameters high; at the end of the one hundred twelfth (112th) traverse, the thickness of the fiber bundle was eight diameters high, etc.

EXAMPLE 4

Two spirally wound, axial flow hollow fiber blood oxygenators were made according to the method described herein. The support cores had the same length and outside diameter as the support cores used in Example 2. The semipermeable hollow fiber had the same outside diameter, wall thickness and mean pore size as the semipermeable hollow fiber used in Example 2. Each inner support core was spirally wound with a fiber ribbon containing one (1) hollow fiber, i.e. a one fiber "ribbon" was used. The fiber was wound at a pitch of about 1.807 inches (4.59 cm.) while maintaining a distance, x, of about 0.0145 inch (0.037 cm.) between adjacent fiber "ribbons" on the core. The fiber band width was 0.033 inch (0.084 cm.) and the ratio of pitch to fiber band width was about 54.8. The wound fiber bundles were about 0.562 inches (1.43 cm.) thick and provided, in the assembled oxygenators, an average effective gas exchange surface area of about 2.76 square meters.

Each support core with the semipermeable hollow fiber wound thereon was assembled into an oxygenator of the type shown and described in the specification and drawings. The two resulting oxygenators were then tested, using bovine blood, in accordance with the AAMI Standard mentioned in Example 1. The average oxygen transfer was determined to be 365 ml/minute at a blood flow of 6 liters/minute; the average oxygen transfer efficiency was therefore 132.2 ml/minute/meter$^2$ (the average oxygen transfer of 365 ml/minute $\div$ the average effective gas transfer area of 2.76 meters$^2$). The average carbon dioxide transfer was determined to be 386 ml/minute at a blood flow of 6 liters/minute and a gas to blood flow ratio of 2; the average carbon dioxide transfer efficiency was therefore 139.9 ml/minute/meter$^2$ (the average carbon dioxide transfer of 386 ml/minute $\div$ the average effective gas transfer area of 2.76 meters$^2$). The average blood phase pressure drop of the two oxygenators during testing was determined to be 154 mmHg at 6 liters/minute blood flow. In this Example 4, the extended inner support core was covered, except for the distance, x, between adjacent portions of the hollow fiber when wound on the core. When the fiber guide on the winding apparatus had traveled a total of one hundred ten (110) traverses, i.e. fifty-five (55) traverses in each direction. The portion of the single fiber of the fiber "ribbon" laid down during the one hundred eleventh (111th) traverse of the fiber guide was in radial registry with the portion of the single fiber of the fiber "ribbon" laid down during the very first traverse of the fiber guide, the portion of the single fiber of the fiber "ribbon" laid down during the two hundred twenty-first (221st) traverse was in radial registry with the portions of the single fiber of the fiber "ribbon" laid down during the first (1st) and one hundred eleventh (111th) traverses, etc.

At the completion of the one hundred tenth (110th) traverse of the fiber guide, the thickness of the fiber bundle on the extended core was equal to two fiber diameters; at the end of the two hundred twentieth (220th) traverse, the thickness of the fiber bundle was four fiber diameters high; at the end of the three hundred thirtieth (330th) traverse, the thickness of the fiber bundle was six fiber diameters high; at the end of the four hundred fortieth (440th) traverse, the thickness of the fiber bundle was eight diameters high, etc.

We claim:

1. A hollow fiber oxygenator, comprising a hollow fiber bundle, would around a supporting core, said supporting core having a first end and a second end and defining an axis extending from said first end to said second end, said hollow fiber bundle comprising hollow, gas permeable fibers each having a first end, a second end and a hollow interior, wherein the first ends of said fibers are adjacent the first end of said core and the second ends of said fibers are adjacent the second end of said core, said fibers including a first plurality of fibers wound helically around said core in a first direction from said first end to said second end of said core, and a second plurality of fibers wound helically around said core in a second direction opposite said first direction from said first end of said core to said second end of said core, whereby said first and second pluralities of fibers intersect one another at an angle measured along the axis of said core;

an outer casing mounted adjacent to and surrounding said fiber bundle;

sealing means for sealing between the first ends of said fibers in said fiber bundle and sealing said fibers to said core and said outer casing;

second sealing means sealing between said second ends of said fibers in said fiber bundle and sealing said fibers to said core and to said outer casing such that said first and second sealing means, said core and said outer casing together define an oxygenator chamber;

a gas inlet operatively coupled to the interior of said fibers at the first ends of said fibers and a gas outlet operatively coupled to the interior of said fibers at the second ends of said fibers; and blood inlet means for allowing blood to enter said oxygenator chamber and blood outlet means for allowing blood to exit from said oxygenator chamber, one of said blood inlet means and said blood outlet means located only adjacent said first ends of said fibers of said fiber bundle, the other of said blood inlet means and said blood outlet means located only adjacent the second ends of said fibers of said fiber bundle, said blood inlet means and said blood outlet means spaced from one another along the axis of said core.

2. An oxygenator according to claim 1 wherein said first plurality of fibers and said second plurality of fibers within said fiber bundle intersect one another at an obtuse angle, as measured along the axis of said core.

3. An oxygenator according to claim 2 wherein said obtuse angle is an angle of about 140° or greater.

4. An oxygenator according to claim 1 wherein said each of said first plurality of fibers and said second plurality of fibers comprises a plurality of fiber ribbons, each of said fiber ribbons comprising one or more of said fibers wound simultaneously throughout the lengths thereof, said fiber ribbons within each of said plurality and second plurality of hollow fibers wound parallel to one another.

5. An oxygenator according to claim 1 wherein said blood inlet means is adjacent said second ends of said fibers in said fiber bundles and wherein said blood outlet means is adjacent said first ends of said hollow fibers in said fiber bundle.

6. An oxygenator according to claim 1 wherein said blood inlet means comprises means for defining an aperture through one of said core and said outer, casing and wherein said blood outlet means comprises means for defining an aperture through the other of said core and said outer casing.

7. An oxygenator according to claim 6 wherein said blood inlet means comprises means for defining an aperture through said core and wherein said blood outlet means comprises means for defining an aperture through said outer casing.

8. An oxygenator according to claim 7 wherein said oxygenator further comprises a heat exchanger chamber containing a heat exchanger means for cooling blood, said heat exchanger chamber provided with a blood entry to and a blood exit from said heat exchanger chamber, the blood exit from said heat exchanger chamber positioned and arranged in fluid communication with said blood inlet means.

9. An oxygenator according to claim 1 wherein the blood entry to said heat exchanger chamber is located below the blood exit from said heat exchange chamber and below said blood inlet means.

10. An oxygenator according to claim 5, 6, 7, 8 or 9 wherein said blood inlet means is located below said blood outlet means.

11. An oxygenator according to claim 5, 6, 7, 8 or 9 wherein said gas inlet is located above said gas outlet.

12. An oxygenator according to claim 1 wherein said hollow fiber bundle comprises a circular cylindrical bundle of hollow fibers and wherein said gas inlet and said gas outlet comprise circular manifolds located adjacent said first and second ends of said fibers of said fiber bundle, respectively.

13. An oxygenator according to claim 1 or claim 12 wherein said blood inlet means and said blood outlet means each comprise means for defining a plurality of inlet and outlet apertures, respectively, arrayed around said fiber bundle adjacent said second and first ends, respectively of said fibers of said fiber bundle, and wherein said blood inlet means and said blood outlet means further comprise circular inlet and outlet manifolds in fluid communication with said pluralities of inlet and outlet apertures.

* * * * *

UNITED STATES PATENT AND TRADEMARK OFFICE
CERTIFICATE OF CORRECTION

PATENT NO. : 4,975,247

DATED : December 4, 1990

INVENTOR(S) : Anthony Badolato, James G. Barrera, and Edmund R. Corey, Jr.

It is certified that error appears in the above-indentified patent and that said Letters Patent is hereby corrected as shown below:

Column 5, Line 32, delete "(2")" and insert in its place --(n/2--.

Column 9, Line 28, delete "450" and insert in its place --40--.

Column 10, Line 67, delete "25B" and insert in its place --15B--.

Column 15, Line 18, after "Example" please insert --1--.

Column 17, Line 46, before first occurence of "plurality" insert --first--.

Column 18, Line 23, delete "claim 1" and insert in its place --claim 8--.

UNITED STATES PATENT AND TRADEMARK OFFICE
CERTIFICATE OF CORRECTION

PATENT NO. : 4,975,247
DATED : December 4, 1990
INVENTOR(S) : Anthony Badolato, et. al.

It is certified that error appears in the above-indentified patent and that said Letters Patent is hereby corrected as shown below:

Column 18, Line 25, delete "exchange" and insert in its place --exchanger--.

Signed and Sealed this

Fourteenth Day of February, 1995

Attest:

BRUCE LEHMAN

*Attesting Officer*     *Commissioner of Patents and Trademarks*